United States Patent [19]

Ranford

[11] Patent Number: 4,998,924
[45] Date of Patent: Mar. 12, 1991

[54] DOUBLE SLEEVE SAFETY SYRINGE

[75] Inventor: Alan B. Ranford, St. Louis, Mo.

[73] Assignee: Sherwood Medical Company, St. Louis, Mo.

[21] Appl. No.: 519,345

[22] Filed: May 2, 1990

Related U.S. Application Data

[63] Continuation of Ser. No. 385,343, Jul. 25, 1989, abandoned.

[51] Int. Cl.⁵ .............................................. A61M 5/32
[52] U.S. Cl. .................................. 604/798; 604/110; 604/192; 604/197; 604/263
[58] Field of Search ............... 604/110, 192, 197–198, 604/263

[56] References Cited

U.S. PATENT DOCUMENTS

| | | |
|---|---|---|
| 2,571,653 | 10/1951 | Bastien . |
| 3,780,734 | 12/1973 | Wulff . |
| 3,890,971 | 6/1975 | Leeson et al. . |
| 4,170,993 | 10/1979 | Alvarez . |
| 4,356,822 | 11/1982 | Winstead-Hall . |
| 4,425,120 | 1/1984 | Sampson et al. . |
| 4,573,976 | 3/1986 | Sampson et al. . |
| 4,631,057 | 12/1986 | Mitchell . |
| 4,643,199 | 2/1987 | Jennings, Jr. et al. . |
| 4,643,200 | 2/1987 | Jennings, Jr. . |
| 4,650,468 | 3/1987 | Jennings, Jr. . |
| 4,655,751 | 4/1987 | Harbaugh . |
| 4,666,435 | 5/1987 | Braginetz . |
| 4,681,567 | 7/1987 | Masters et al. . |
| 4,693,708 | 9/1987 | Wanderer et al. . |
| 4,695,274 | 9/1987 | Fox . |
| 4,723,943 | 1/1988 | Spencer .................. 604/198 |
| 4,737,144 | 4/1988 | Choksi . |
| 4,743,233 | 5/1988 | Schneider . |
| 4,813,426 | 3/1989 | Haber et al. ............. 604/198 X |
| 4,842,587 | 6/1989 | Poncy . |
| 4,874,383 | 10/1989 | McNaughton . |
| 4,892,107 | 1/1990 | Haber ...................... 604/110 X |

FOREIGN PATENT DOCUMENTS

| | | |
|---|---|---|
| A1216460 | 4/1987 | European Pat. Off. . |
| A2240987 | 10/1987 | European Pat. Off. . |
| A1250104 | 12/1987 | European Pat. Off. . |
| A2252644 | 1/1988 | European Pat. Off. . |
| 2833804 | 3/1979 | Fed. Rep. of Germany . |
| 8606355 | 10/1986 | Fed. Rep. of Germany . |
| 3609516 | 6/1987 | Fed. Rep. of Germany . |
| 2624023 | 6/1989 | France .................... 604/198 |

*Primary Examiner*—C. Fred Rosenbaum
*Assistant Examiner*—Corrine Maglione
*Attorney, Agent, or Firm*—Andrew J. Beck; Montgomery W. Smith; Richard D. Allison

[57] ABSTRACT

An improved safety syringe is disclosed herein comprising a locating ring positioned on the distal end of a syringe barrel and a pair of first and second sleeves which interact with a projecting tab on the locating ring to movably retain the first sleeve in retracted and extended positions and wherein in the extended position one of the sleeves enclose the syringe needle in an irreversible locked arrangement.

32 Claims, 6 Drawing Sheets

DOUBLE SLEEVE SAFETY SYRINGE

This is a continuation of copending application Ser. No. 385,343, filed on July 25, 1989, now abandoned.

FIELD OF THE INVENTION

This invention relates to safety syringes and more particularly to an improved safety syringe having a locating ring, a split sleeve and an outer locking ring.

BACKGROUND OF THE INVENTION

The majority of syringes used today for medical or laboratory purposes are disposable and are intended to be discarded after a single use. Disposal of these syringes poses a potential hazard for the individuals who use the syringes, as well as for those who dispose of them. With the increased awareness concerning the potential for the transmission of AIDS and other infectious diseases, a number of different devices have been proposed to prevent accidental needle sticks or to otherwise disable the syringe after a single use.

One approach to this problem is to provide a retractable shield which is movable between a retracted position and an extended position. A common feature of these syringes is that when the retractable shield is moved to the extended position, the shield covers the needle and cannot be retracted without the use of extraordinary force.

A number of such constructions have been proposed to satisfy the general requirement that the needle be permanently covered after the syringe has been used. Some of these constructions involve twist-to-lock mechanisms which often require at least two hands to operate and do not readily indicate when the shield has been locked into the extended position. Other syringes lock automatically when the shield is extended. In many of these syringes, the locking mechanism remains exposed and may be manually manipulated to retract the shield after the shield has been "irreversibly" locked.

These devices meet the general requirements for a safety syringe; however, many of them are much too complicated to manufacture economically and efficiently. Certain of these devices require extensive modification of the standard syringe components. This is generally unacceptable due to the large investment most manufacturers have in their present molding and extrusion equipment. Other devices cannot realistically be mass produced using presently known manufacturing techniques. Finally, certain other devices require a large number of manipulative steps during their assembly and thus a large amount of manual labor and cannot be economically mass produced.

Therefore, it is apparent that a need remains for a safety syringe having a retractable shield which is movable between an accessible retracted position and a reliable extended position, and which may be mass produced efficiently and economically.

SUMMARY OF THE PRESENT INVENTION

An object of the present invention is to substantially overcome the disadvantages mentioned above.

Another object of the present invention is to provide a safety syringe which performs all of the general requirements of this type of syringe and which cannot be readily manipulated to defeat the locking mechanism once the retractable shield is placed in the extended position.

A further object of the present invention is to provide a safety syringe which is improved in the functional utility and ease of manufacture of the protective retractable shield.

A further object of the present invention is to provide a safety syringe which is inexpensive to manufacture using existing manufacturing methods and equipment.

In accordance with the present invention, a split sleeve or retractable shield is mounted on a standard syringe barrel. The sleeve is movable between a retracted position in which the needle is exposed and an extended position in which the sleeve extends beyond the distal end of the barrel to protect the needle. The sleeve includes a longitudinal slot therein which extends at least partially along one side thereof. The present invention also includes a locating ring attached to the distal end of the barrel adjacent to the needle hub. The locating ring includes at least one positioning tab extending outwardly therefrom generally perpendicular to the lengthwise dimension of the split sleeve. A locking ring is movably positioned on the split sleeve to selectively engage the positioning tab and compress the split sleeve therebetween.

In the first embodiment of the present invention, the locating ring is press-fit onto the distal end of the syringe barrel. The locating ring includes an annular ring and an outwardly extending locking tab to assist in the alignment and orientation of the split sleeve. The split sleeve of this embodiment includes a longitudinal slot extending along the entire length thereof. An outer sleeve is movably positioned on the proximal end of the split sleeve and selectively engages one or more of the ridges and grooves located on the proximal end of the split sleeve.

The second embodiment is similar to the first embodiment of the present invention. As with the first embodiment, the second embodiment includes a locating ring press-fit onto the distal end of the syringe barrel and includes an outwardly extending locking tab thereon to assist in the alignment of the split sleeve. The split sleeve includes a longitudinal slot along the entire length thereof and a pair of locking rings located near the proximal end of the split sleeve. The outer sleeve of this embodiment is movably positioned on the proximal end of the split sleeve and includes an oval-shaped inner diameter to selectively compress the split sleeve as the outer sleeve is rotated about the split sleeve to retain the locking tab therein.

The third embodiment of the present invention includes a locating ring similar to the locating ring of the second embodiment. The split sleeve of this embodiment includes a longitudinal slot which extends from the distal end of the split sleeve to a location beyond the mid-point of the split sleeve. The outer sleeve is initially positioned on the distal end of the split sleeve and is movable proximally along the split sleeve to a location proximal to the longitudinal slot.

An advantage of the present invention is that it is simple to operate and efficiently protects the user of the syringe from accidental needle sticks.

A further advantage of the present invention is that it is readily adaptable for use on a variety of standard syringes.

A further advantage of the present invention is that it is inexpensive to manufacture and assemble.

BRIEF DESCRIPTION OF THE DRAWINGS

FIG. 12 is a cross-sectional view taken along lines 12—12 of FIG. 11;

FIG. 13 is a cross-sectional view taken along lines 13—13 of FIG. 11;

FIG. 14 is a side view, partially in cross-section, of the outer sleeve of the alternate embodiment illustrated in FIG. 8;

FIGS. 15A and B are end views of the outer sleeve of the alternate embodiment illustrated in FIG. 8;

DETAILED DESCRIPTION OF THE PREFERRED EMBODIMENTS

In the preferred embodiment, the invention is intended to be used in conjunction with a conventional syringe; however, the split sleeve and outer sleeve of the present invention are readily adaptable for use on nearly any medical or laboratory device having an elongate section or barrel and a needle, such as a blood collection tube having a double-ended needle. Accordingly, as used herein, the term "syringe" is intended to include any medical or scientific device utilizing a needle wherein it is desired to protect a user from accidental needle sticks.

In describing the present invention, the term "distal end" of an element refers to the end of the element closest to the needle point. The term "proximal end" of an element refers to the end of the element furthest from the needle point. The term "retracted position" refers to the position of the split sleeve wherein the needle is exposed and the split sleeve is adjacent to the barrel of the syringe. The term "extended position" refers to the position of the split sleeve wherein at least part of the split sleeve extends distally beyond the end of the barrel of the syringe and the needle is covered by the split sleeve.

The present invention is described herein with particular reference to a conventional syringe. The conventional syringe is comprised of an elongate tubular barrel 10 having a proximal flange 11, a plunger 12 slidable within the barrel 10, and a needle assembly 13 through which the contents of the barrel 10 are dispensed when the plunger 12 is moved distally within the barrel 10. The needle assembly 13 comprises a needle 14 having a sharpened needle tip 15 and a hub 16 at the proximal end of the needle assembly 13.

A conically shaped luer tip (not shown) and a luer lock skirt 18 are integrally formed at the distal end of the barrel 10 with the luer lock skirt 18 encircling the luer tip (not shown). The interior surface of the luer lock skirt 18 includes internally oriented threads adapted to threadedly engage complementary ridges on the needle hub 16. The exterior surface of the luer lock skirt 18 frictionally contacts and engages the locating ring 50 of the present invention.

As illustrated in FIGS. 1-7, the first embodiment of the present invention consists generally of a split sleeve 30, a locating ring 50 and an outer sleeve 70. The locating ring 50 is press-fit, adhesively bonded or welded to the distal end of the syringe barrel 10 and engages the external surface of the luer lock skirt 18. The split sleeve 30 is a generally elongate tubular sleeve which slideably fits over the syringe barrel 10. The outer sleeve 70 is rotatably mounted on the split sleeve 30 and is movable between retracted and extended positions.

Figure 3:
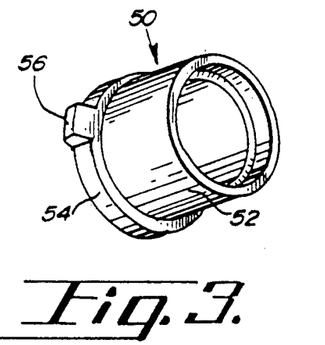
FIG. 3 is a perspective view, partially in cross-section, of the locating ring of the present invention.

The locating ring 50 of the first embodiment is preferably constructed of a rigid polycarbonate plastic and includes a cylindrical body section 52 having a distally positioned annular ring 54 and a locking tab 56 extending therefrom. The locking tab 56 extends outwardly from the annular ring 54 a sufficient distance to cooperate with the split sleeve 30 in the retracted and extended positions. A locking ridge 58 is positioned on the inner surface of the locating ring 50 to contact the outer surface of the luer lock skirt 18 and retain the location ring 50 thereon. The annular ring 54 extends outwardly from and perpendicular to the body 52 of the locating ring 50 to support the interior of the split sleeve 30 as the split sleeve 30 is moved between the retracted and extended positions.

Figure 4:
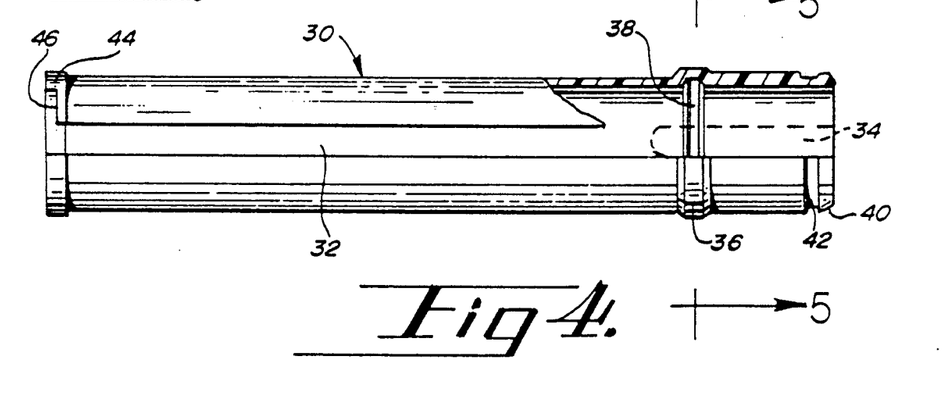
FIG. 4 is a side view, partially in cross-section, of the split sleeve of the present invention.
Figure 5:
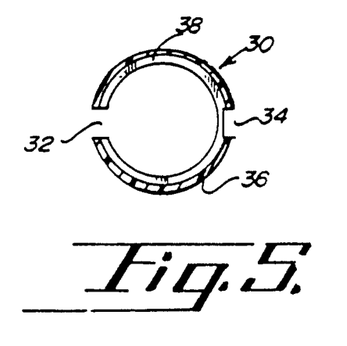
FIG. 5 is a cross-sectional view of the split sleeve taken along lines 5—5 of FIG. 4.

The split sleeve 30 is a generally elongate tubular sleeve preferably constructed of a rigid polypropylene plastic. The split sleeve 30 includes a longitudinal slot 32 extending along and through one side thereof from the proximal end to the distal end. An orientation channel 34 is located on the inner surface of the split sleeve 30 opposite the longitudinal slot 32. The orientation channel 34 extends inwardly from the proximal end of the split sleeve 30 to a location slightly beyond the annular locking ring 36. The annular locking ring 36 is located inwardly from the proximal end of the split sleeve 30 and includes a tab retaining groove 38 extending along the entire inner surface thereof. The outer surface of the proximal end of the split sleeve 30 includes a bevelled end 40 and an annular sleeve retaining groove 42 positioned adjacent and distally to the bevelled end 40 on the outer surface of the split sleeve 30. The distal end of the split sleeve 30 includes a flanged ring 44 having an enlarged diameter and a partial channel 46 along the distal surface thereof. The partial channel 46 is in communication with the longitudinal channel 32 and retains the locking tab 56 therein when the split sleeve 30 is in the retracted position.

Figure 6:
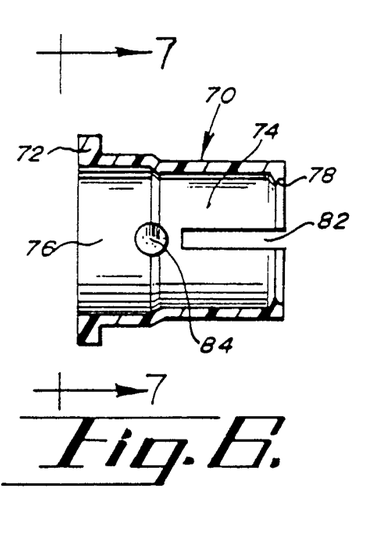
FIG. 6 is a cross-sectional view of the outer sleeve of the present invention.
Figure 7:
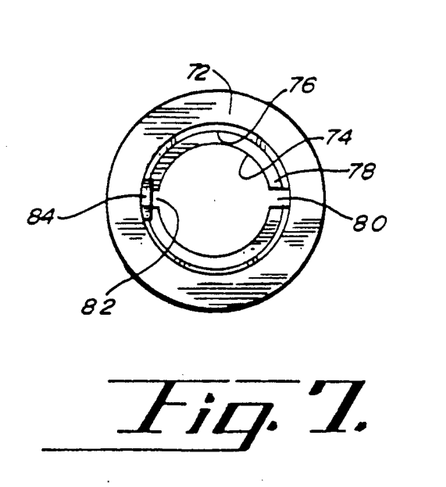
FIG. 7 is an end view of the outer sleeve of the present invention taken along lines 7—7 of FIG. 6.

The outer sleeve 70 is slidably positioned on the proximal end of the split sleeve 30 and is preferably constructed of a rigid polypropylene plastic. The outer distal surface of the outer sleeve 70 includes an enlarged annular flange 72 to assist in the movement of the outer sleeve 70 and split sleeve 30 along the syringe barrel 10 lengthwise between the retracted and extended positions. The inner surface of the outer sleeve 70 includes first and second sections, 74 and 76 respectively, wherein the first section 74 is proximal to the second section 76 and has a smaller inner diameter than the second section 76. The proximal end of the outer sleeve 70 includes an inwardly directed annular lip 78 adjacent to the first section 74. A pair of expansion slots, 80 and 82 respectively, extend distally from the proximal end of the outer sleeve 70 along nearly the entire length of the first section 74. An inwardly projecting orientation key 84 is located on the proximal end of the second section 76 and adjacent to the distal end of the first section 74 and extends inwardly to a location beyond the inner diameter of the first section 74.

Figure 1:
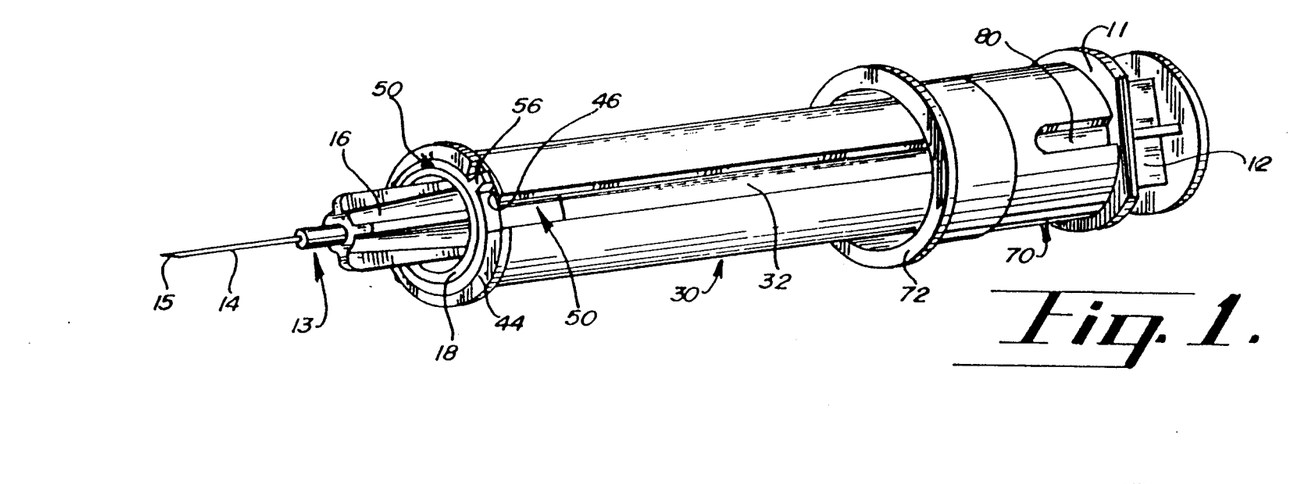
FIG. 1 is a perspective view of the present invention in the retracted position.

The first embodiment is preferably assembled and stored in the retracted position. The split sleeve 30 is releaseably held in the retracted position by the locking tab 56 which extends outwardly from the locating ring 50 to contact the partial channel 46 on the flanged ring 44. The outer sleeve 70 is movably located on the proximal end of the split sleeve 30 so that the annular lip 78 is positioned between the bevelled end 40 of the split sleeve 30 and the proximal flange 11 of the syringe barrel 10. The outer sleeve 70 is prevented from rotational movement along the split sleeve 30 by the orientation key 84 which is slidably aligned in the orientation channel 34.

Figure 2:
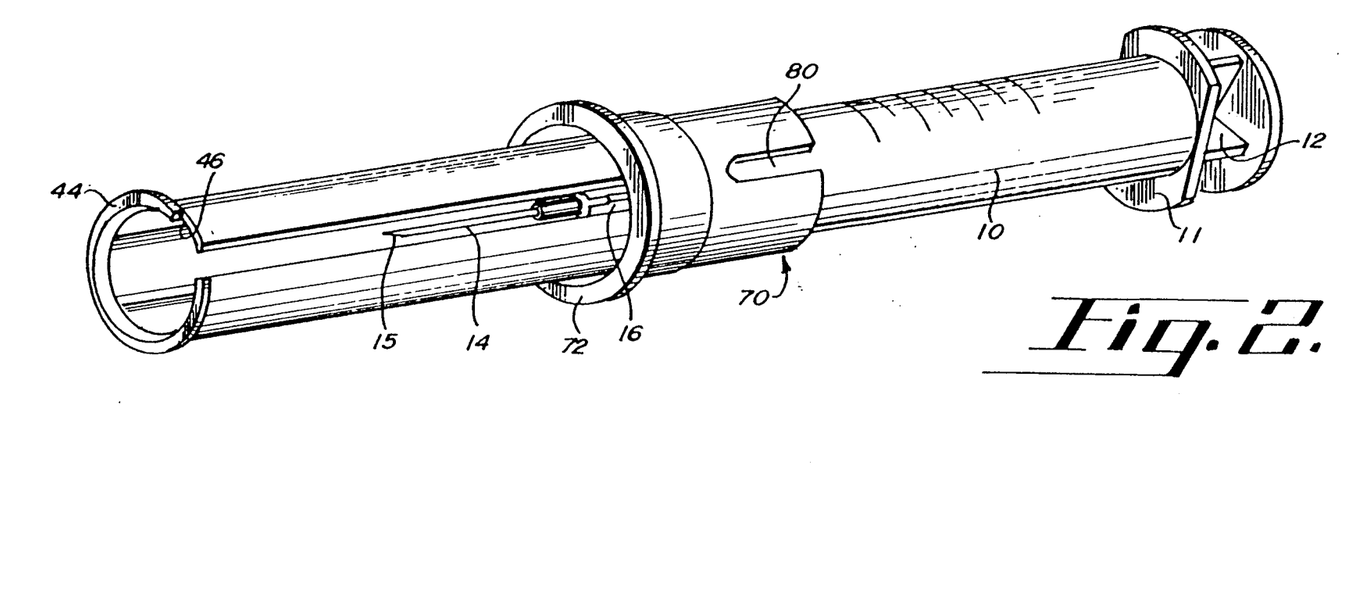
FIG. 2 is a perspective view of the present invention in the extended position.

In order to move the split sleeve 30 from the retracted position to the extended position, the split sleeve 30 is first rotated clockwise by grasping the annular flange 72 on the outer sleeve 70 and rotating the split sleeve 30 and outer sleeve 70 until the locking tab 56 is moved from the partial channel 46 into the longitudinal slot 32. The split sleeve 30 and outer sleeve 70 are then moved distally along the syringe barrel 10 until the annular ring 54 contacts the retaining groove 38 located on the inner surface of the split sleeve 30. The split sleeve 30 is then locked in the extended position by grasping the annular flange 72 on the outer sleeve 70 and sliding the outer sleeve 70 distally over the proximal end of the split sleeve 30. As this occurs, the annular lip 78 is forced over the bevelled end 40 of the split sleeve 30 causing the proximal end of the outer sleeve 70 to expand as permitted by the expansion slots 80 and 82. The outer sleeve 70 moves distally along the split sleeve 30 until the annular lip 78 contacts and becomes irreversibly engaged in the sleeve retaining groove 42. In this extended position, the retaining groove 38 encompasses the annular ring 54 of the locating ring 50 and the split sleeve 30 can no longer advance. Additional forward pressure on the outer sleeve 70 causes the annular lip 78 to ride up over the bevelled end 40 of the split sleeve 30 and then drop into the sleeve retaining groove 42. When the outer sleeve 70 is in this position, the second section 76 of the outer sleeve 70 envelops the annular locking ring 36 to prevent the split sleeve 30 from opening, thus locking the split sleeve 30 in position on the annular ring 54 of the locating ring 50. When the outer sleeve 70 is moved to the locking position, the split sleeve 30 cannot be returned to the retracted position unless extraordinary force is used to move the outer sleeve 70 and split sleeve 30 proximally along the syringe barrel 10.

As illustrated in FIGS. 8-15, the second embodiment consists generally of a locating ring 90, a split sleeve 100 and an outer sleeve 120. The locating ring 90 of this embodiment is preferably constructed of a rigid polycarbonate plastic and includes a cylindrical body section 92 and an outwardly extending locking tab 94 extending from the distal end of the locating ring 90. As with the first embodiment, the locating ring 90 may be either press-fit onto the distal end of the syringe barrel 10 through the use of a locking ridge 96 on the inner surface of the locating ring or the locating ring 90 may be adhesively bonded or welded to the distal end of the syringe barrel 10 to engage the external surface of the luer lock skirt 18. In this embodiment, the locking tab 94 is larger than in the first embodiment and the annular ring has been eliminated.

Figure 11:
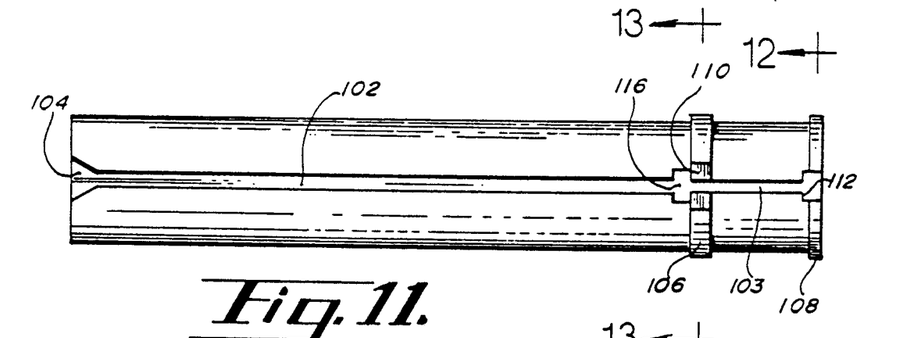
FIG. 11 is a side view of the split sleeve of the alternate embodiment illustrated in FIG. 8.

The split sleeve 100 of this embodiment is a generally elongate tubular sleeve which is preferably constructed of a rigid polypropylene plastic. The split sleeve 100 slideably surrounds the syringe barrel 10 and includes a lengthwise longitudinal slot 102 extending along and through one side thereof from the proximal end to the distal end. The distal end of the longitudinal slot 102 includes an enlarged tapered opening 104 therein to releaseably retain the locking tab 94 within the tapered opening 104 when the split sleeve 100 is in the retracted position. The proximal end of the longitudinal slot 102 includes a compressible section 103 therein to prevent the passage of the locking tab 94 therethrough.

Figures 12, 13, 14, 15A, 15B:
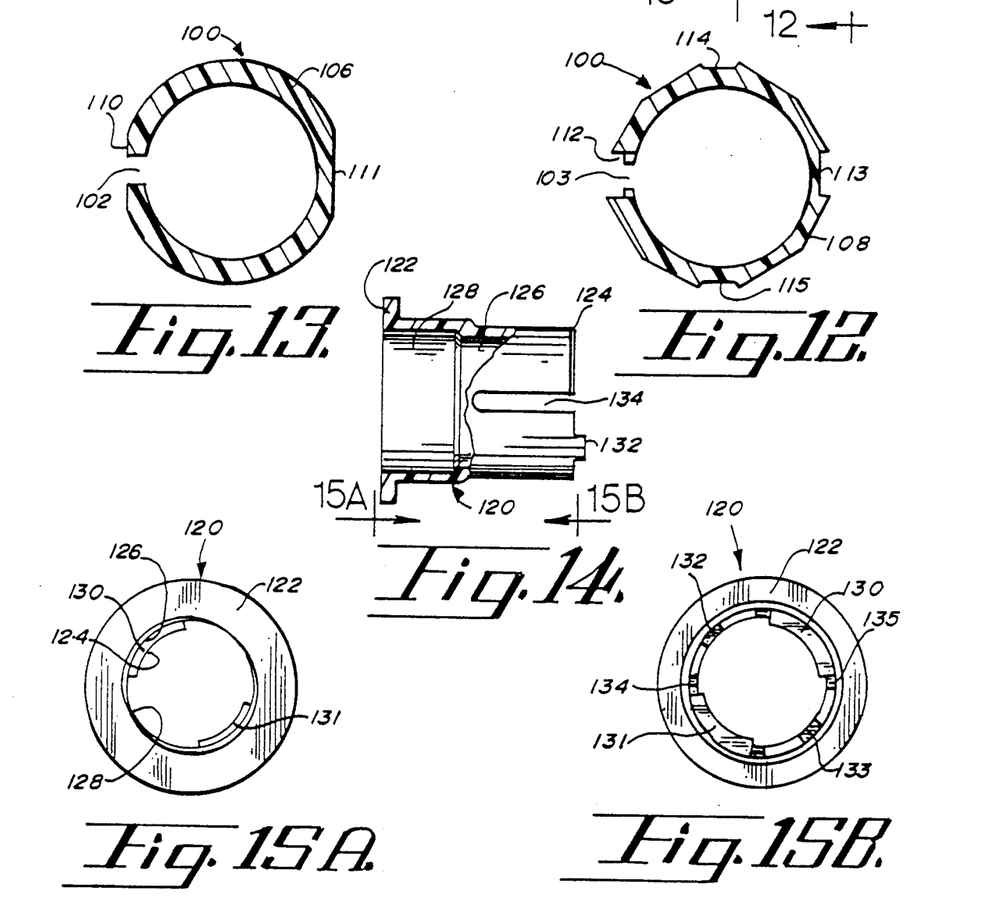

The proximal end of the split sleeve 100 includes a pair of annular rings, 106 and 108, respectively, on the outer surface thereof. The first annular ring 106 is spaced distally from the second annular ring 108 on the proximal end of the split sleeve 100. The first annular ring 106 is generally circular and extends outwardly perpendicular to the lengthwise dimension of the split sleeve 100. A pair of opposed flat surfaces, 110 and 111 respectively, are located on the outer surface of the first annular ring 106 to provide additional flexibility to the split sleeve 100. The first flat surface 110 forms a generally flat surface adjacent to the proximal end of the longitudinal slot 102. The second flat surface 111 is located on the side of the first annular ring 106 opposite to the first flat surface 110 and comprises a generally flat surface on the otherwise circularly shaped first annular ring 106. A tab retaining slot 116 is located on the distal side of the first annular ring 106 and forms an enlarged, generally rectangular opening in the longitudinal slot 102 to retain the locking tab 94 therein when the split sleeve 100 is in the extended position.

The second annular ring 108 is a dodecagonally shaped locking ring located on the proximal end of the split sleeve 100 and includes a pair of oppositely oriented positioning grooves, 112 and 113 respectively. The first positioning groove 112 is located adjacent to the longitudinal slot 102 to form a generally rectangular groove therein. The second positioning groove 113 is located on the opposite side of the locking ring 108 and also forms a generally rectangular groove. A second pair of positioning grooves, 114 and 115 respectively, are oriented perpendicular to the first pair of positioning grooves, 112 and 113. The second pair of positioning grooves 114 and 115, respectively, consist of inwardly tapered grooves to releasably engage the retaining tabs 132 and 133 on the outer sleeve 120.

The outer sleeve 120 of this embodiment is positioned on the proximal end of the split sleeve 100 and is preferably constructed of a rigid polypropylene plastic. The outer distal surface of the outer sleeve 120 includes an enlarged annular flange 122 to assist in the movement of the outer sleeve 120 and the split sleeve 100 between the retracted and extended positions. The inner surface of the outer sleeve 120 consists generally of first, second and third sections designated herein generally as 124, 126 and 128, respectively. The first section 124 is located at the proximal end of the split sleeve 100 and includes a pair of opposed inwardly directed retaining rims, 130 and 131, and a pair of opposed longitudinally extending retaining tabs, 132 and 133. A pair of opposed expansion slots, 134 and 135, extend distally from the proximal end of the split sleeve 100, through the first section 124 and into the second section 126. The inner surface of the second section 126 is preferably cylindrical and has an inner diameter larger than the first section 124. The inner surface of the second section 126 is smaller than the inner diameter of the third section 128. The inner diameter of the third section 128 is oval shaped with the axis of the major diameter of the oval in alignment with the retaining tabs 131 and 132.

Figures 8, 9:
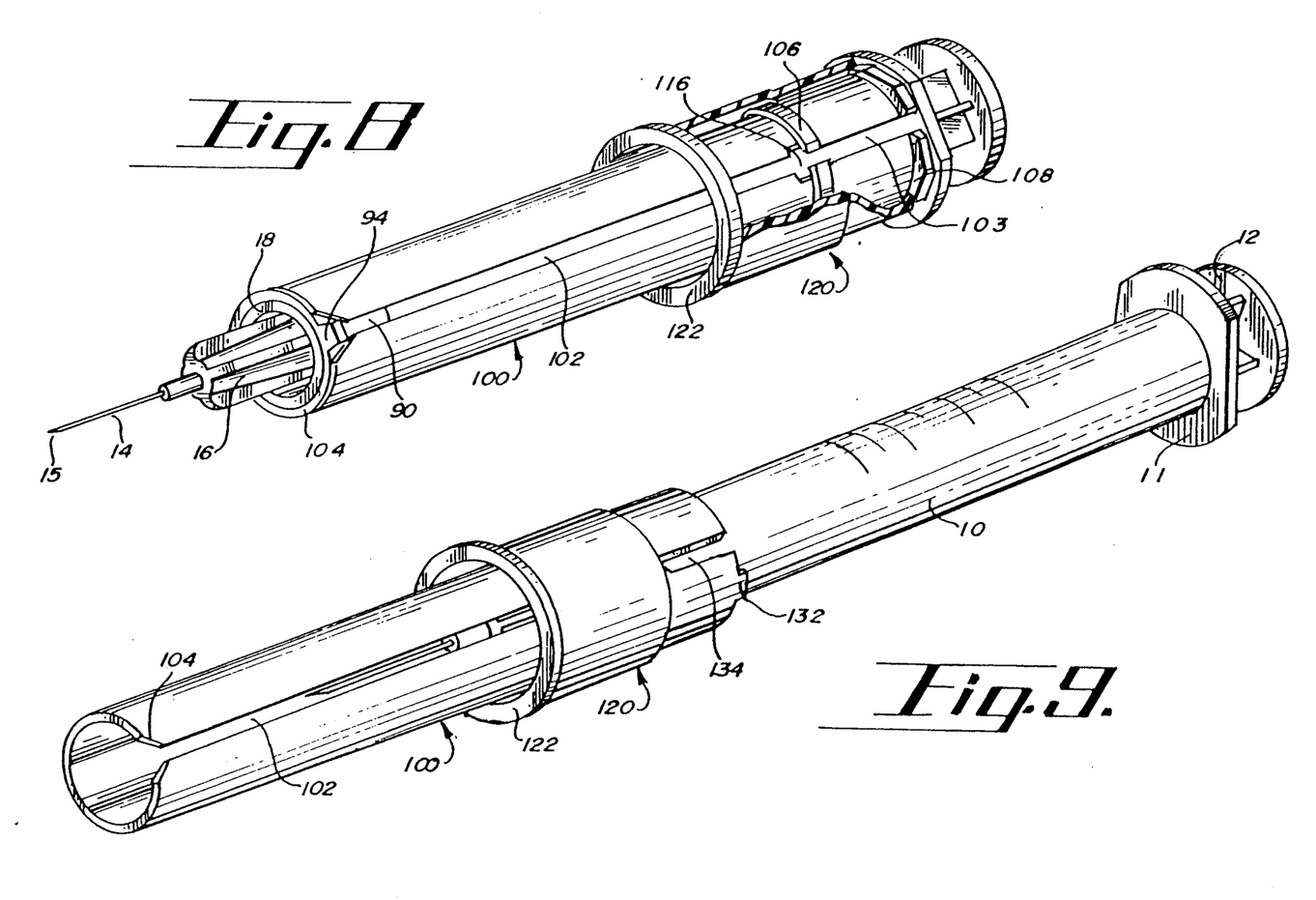
FIG. 8 is a perspective view of an alternate embodiment of the present invention in the retracted position.
FIG. 9 is a perspective view of the alternate embodiment of FIG. 8 illustrated in the extended position.
Figure 10:
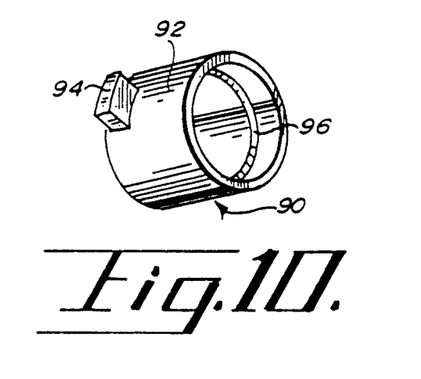
FIG. 10 is a perspective view of the locating ring of the alternate embodiment illustrated in FIG. 8.

The second embodiment is preferably assembled and stored in the retracted position. The split sleeve 100 is releaseably held in the retracted position by the locking tab 94 which is frictionally held in the tapered opening 104 of the longitudinal slot 102. The outer sleeve 120 is movably positioned on the split sleeve 100 so that the retaining rims 130 and 131 are distal to the locking ring 108. The retaining tabs 132 and 133 are oriented to be biased outwardly in the positioning grooves 114 and 115 on the locking ring 108 and the second section 126 of the outer sleeve 120 is proximal to the first annular ring 106.

In order to move the split sleeve 100 from the retracted position to the extended position, the user grasps the annular flange 122 to move the outer sleeve 120 and the split sleeve 100 distally along the syringe barrel 10. As the split sleeve 100 moves distally along the barrel 10 through the tapered opening 104, the locking tab 94 causes the longitudinal slot 102 and split sleeve 100 to expand. This occurs because of the clearance between the outside diameter of the split sleeve 100 and the inside diameter of the outer sleeve 120 at the second section 126. Additionally, the orientation of the oval shaped inner diameter of the third section 128 in the outer sleeve 120 allows the first annular ring 106 to expand a limited amount. Once the locking tab 94 reaches the tab retaining slot 116, the split sleeve 100 springs closed and is prevented from further distal movement.

In order to lock the split sleeve 100 in the extended position, the outer sleeve 120 is rotated clockwise or counterclockwise until the retaining tabs, 132 and 133, engage the first and second positioning grooves, 112 and 113, respectively. The locking tab 94 is then retained in the tab retaining slot 116 and the elliptically shaped second section 126 causes the outer sleeve 120 to compress the proximal end of the split sleeve 100. The outer sleeve 120 is prevented from moving proximally along the split sleeve 100 by the retaining rims, 130 and 131, which engage the distal side of the locking ring 108.

As illustrated in FIGS. 16-21, the third embodiment of the present invention consists generally of a split sleeve 150, a locating ring 170 and an outer sleeve 180. The locating ring 170 is preferably press-fit by using a locking ridge 176 on the inner surface of the locating ring 170 or the locating ring 170 may be adhesively bonded or welded to the distal end of the syringe barrel 10 to engage the external surface of the luer lock skirt 18. The split sleeve 150 is a generally elongate tubular sleeve which slideably fits over the syringe barrel 10. The outer sleeve 180 is rotatably mounted on the split sleeve 150.

Figures 17, 18:
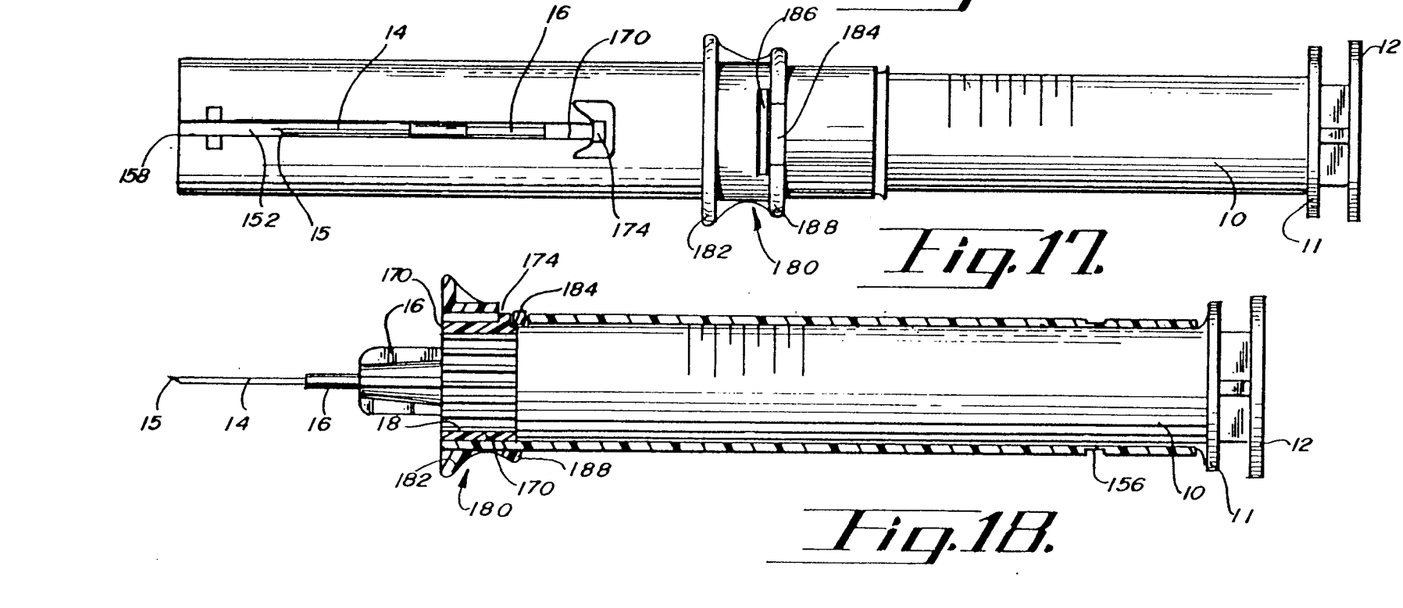
FIG. 17 is a side view of the alternate embodiment illustrated in FIG. 16 in the extended position.
FIG. 18 is a cross-sectional view of the alternate embodiment illustrated in FIG. 16.
Figure 19:
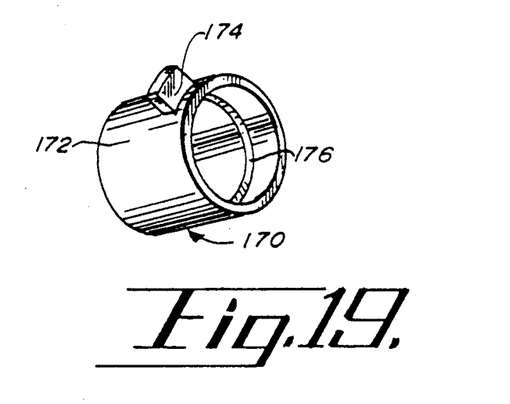
FIG. 19 is an end view of the embodiment illustrated in FIG. 16.

The locating ring 170 of this embodiment is similar to the locating ring 90 of the second embodiment and is preferably constructed of a rigid polycarbonate plastic. The locating ring 170 consists of a cylindrical body section 172 and a locking tab 174 positioned near the proximal end of the body section 172. The locking tab 174 extends outwardly from the body section 172 a sufficient distance to pass through the split sleeve 150 and has a peripheral radius generally equal to the outer radius of the split sleeve 150.

Figure 16:
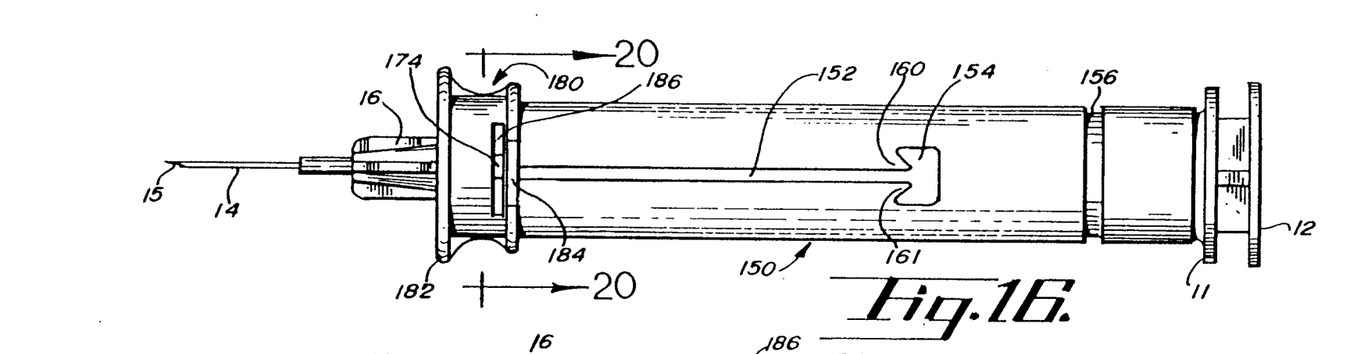
FIG. 16 is a side view of another alternate embodiment of the present invention in the retracted position.

The split sleeve 150 of this embodiment is preferably constructed of a rigid polypropylene plastic. The split sleeve 150 includes a longitudinal slot 152 which extends proximally from the distal end of the split sleeve 150 to a proximal U-shaped enlarged slot 154 located near the proximal end of the split sleeve 150. An annular groove 156 is located on the outer surface of the split sleeve 150 between the enlarged slot 154 and the proximal end of the split sleeve 150.

Figure 20:
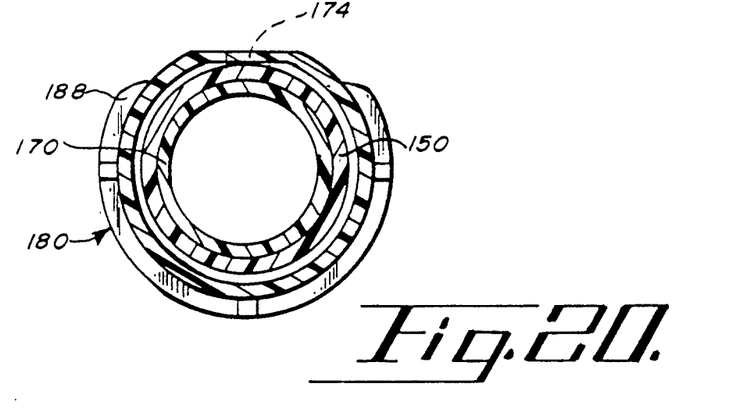
FIG. 20 is an end view, partially in cross section, of the outer sleeve taken along lines 20—20 of FIG. 16.
Figure 21:
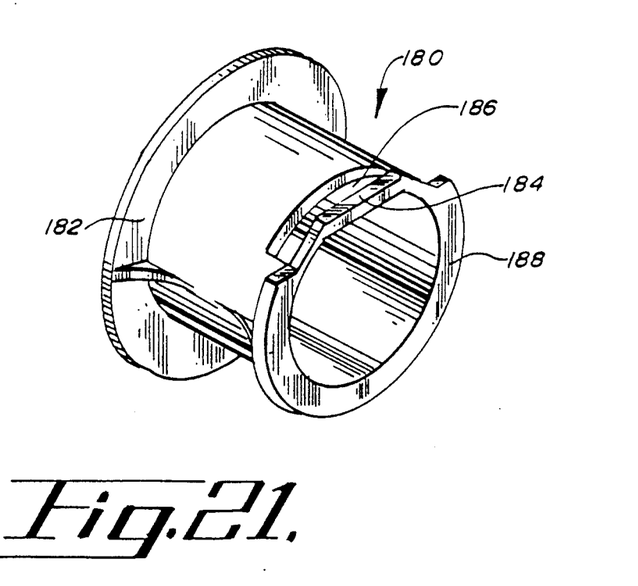
FIG. 21 is a perspective view of the outer sleeve of the alternate embodiment illustrated in FIG. 16.

The outer sleeve 180 of this embodiment is preferably constructed of a rigid polypropylene plastic and includes an annular flange 182 on the distal end thereof to facilitate the movement of the outer sleeve 180 and split sleeve 150 between the retracted and extended positions. The proximal end of the outer sleeve 180 includes a flexible hinge 184, a tab retaining slot 186 located immediately distal of the flexible hinge 184 and a partial flange 188 located adjacent to the flexible hinge 184 on the proximal end of the outer sleeve 180.

This embodiment is preferably assembled and stored in the retracted position. The split sleeve 150 is releaseably held in the retracted position by the outer sleeve 180 which contacts the flattened groove 158 on the distal end of the split sleeve 150. The flexible hinge 184 of the outer sleeve 180 forms a generally flat area on the otherwise circular inner surface of the outer sleeve 180. This flat surface contacts the tapered flattened groove 158 on the split sleeve 150 and retains the locking tab 17 in the tab retaining slot 186.

In order to move the split sleeve 150 from the retracted to the extended position, the outer sleeve 180 is grasped by the user and rotated approximately one-eighth turn. This releases the locking tab 174 from the tab retaining slot 186 and allows the outer sleeve 180 to be moved proximally along the split sleeve 150 until the outer sleeve 180 reaches the annular groove 156. When the outer sleeve 180 reaches the annular groove 156, the flat surface on the flexible hinge 184 irreversibly retains the outer sleeve 180 near the proximal end of the split sleeve 150. The split sleeve 150 is then moved distally along the syringe barrel 10 by grasping the annular flange 182 on the outer sleeve 180. The split sleeve 150 is moved distally along the syringe barrel 10 until the locking tab 174 engages the enlarged slot 154 on the proximal end of the longitudinal slot 152. Once this occurs, the locking tab 174 is prevented from moving distally in the longitudinal slot 150 by a pair of flexible extensions, 160 and 161, formed by the enlarged slot 154. The flexible extensions, 160 and 161, are designed to be biased inwardly towards the longitudinal slot 152 and cannot be easily manipulated to release the split sleeve 150 from the extended position.

The foregoing is intended to be illustrative of the preferred embodiments of the present invention and is not intended to limit the scope of the present invention as defined by the following claims.

What is claimed is:

1. A safety syringe, comprising
a syringe having proximal and distal ends and including a generally elongate tubular barrel section extending therebetween, and a needle attached to the distal end of the barrel section,
a locating ring having a body section attached to the distal end of said barrel section and including an outwardly extending projecting means extending therefrom,
an elongate first sleeve having proximal and distal ends movable over said barrel section and locating ring between a retracted position wherein the needle is exposed and an extended position wherein said first sleeve surrounds the needle, said first sleeve including an elongate slot therein extending proximally from the distal end of said first sleeve and wherein the projecting means of said locating ring extends therethrough, and
a second sleeve having proximal and distal ends and which is movable over said first sleeve wherein said second sleeve cooperates with said projecting means on said locating ring to retain the first sleeve therebetween in the extended position.

2. The syringe of claim 1, wherein the elongate slot extends from the distal end of the first sleeve to the proximal end of said first sleeve and wherein said second sleeve compresses said first sleeve about said projecting means to retain said first sleeve in the extended position.

3. The syringe of claim 1, wherein the projecting means contacts said first sleeve to retain said first sleeve in the retracted position.

4. The syringe of claim 1, wherein said first sleeve includes an inner annular groove therein to retain said projecting means therein when said first sleeve is in the extended position.

5. The syringe of claim 4, wherein the second sleeve is movable about the proximal end of said first sleeve to retain the first sleeve in the extended position.

6. The syringe of claim 4, wherein said first sleeve is releasable from the retracted position by rotational movement of said first sleeve about said barrel section and wherein said first sleeve is rotatable about said projecting means when said first sleeve is in the extended position.

7. The syringe of claim 5, wherein said second sleeve is rotationally fixed about said first sleeve.

8. The syringe of claim 1, wherein the second sleeve engages the projecting means on the locating ring and retains the first sleeve in the retracted position.

9. A safety device, comprising
a device having proximal and distal ends and a generally tubular barrel section extending therebetween, and a needle attached to the distal end of the barrel section,
a locating ring attached to the distal end of said barrel section,
an elongate first sleeve having proximal and distal ends movable over said barrel section and locating ring and including a longitudinal slot extending proximally from the distal end thereof and wherein said first sleeve is movable between a retracted position wherein said needle is exposed and an extended position wherein the first sleeve surrounds the needle,
a second sleeve having proximal and distal ends movable over said first sleeve and said barrel section and wherein the second sleeve retains the proximal end of said first sleeve in the extended position, and
a projecting means extending between the locating ring and the first sleeve to retain the first sleeve in the retracted and extended positions.

10. The device of claim 9, wherein the proximal end of the second sleeve extends beyond the proximal end of the first sleeve in the retracted position and is movable distally along the first sleeve when the first sleeve is in the extended position and wherein the second sleeve is rotationally fixed to the first sleeve.

11. The device of claim 9, wherein the projecting means extends outwardly from the locating ring into a perpendicular slot groove located on the first sleeve when the first sleeve is in the extended position.

12. The device of claims 9, wherein the projecting means extends outwardly from the locating ring into an annular groove located on the second sleeve when the first sleeve is in the extended position.

13. The device of claim 9, wherein the longitudinal slot extends from the proximal end to the distal end of the first sleeve and further includes a retaining slot therein to retain the projecting means therein when the first sleeve is in the extended position.

14. The device of claim 9, wherein an enlarged ring on the first sleeve cooperates with the inner surface of the second sleeve to compress the proximal end of the first sleeve when the first sleeve is in the extended position.

15. A safety syringe, comprising
a syringe having proximal and distal ends and a barrel section extending therebetween, a plunger slidable within the barrel section, and a needle attached to the distal end of the barrel section,
a locating ring attached to the distal end of the barrel section and including a projecting means extending outwardly therefrom,
an elongate first sleeve having proximal and distal ends movable over said barrel section and locating ring between a retracted position wherein the needle is exposed and an extended position wherein the needle is surrounded, said first sleeve including an elongate slot therein extending proximally from the distal end of said first sleeve and wherein said projecting means extends therethrough, and
a second sleeve having proximal and distal ends movably positioned on said first sleeve wherein said second sleeve cooperates with said locating ring to retain and compress the first sleeve therebetween in the extended position.

16. The syringe of claim 15, wherein the projecting means contacts the distal end of the elongate slot on the first sleeve to retain the first sleeve in the retracted position.

17. The syringe of claim 16, wherein the projecting means is retained in a second slot on the first sleeve when the first sleeve is in the extended position and wherein the second sleeve compresses the proximal end of the first sleeve when the first sleeve is in the extended position.

18. The syringe of claim 15, wherein the first sleeve and second sleeve are movable between a retracted position, a reversible extended position and an extended locked position wherein the first sleeve irreversibly surrounds the needle.

19. The syringe of claim 18, wherein distal movement of the second sleeve about the first sleeve causes the second sleeve to irreversibly retain the first sleeve in the extended locked position.

20. The syringe of claim 18, wherein rotational movement of the second sleeve about the first sleeve causes the second sleeve to irreversibly retain the first sleeve in the extended locked position.

21. The syringe of claim 18, wherein the proximal end of the second sleeve includes a locking means thereon to prevent the rotational movement of the second sleeve about the first sleeve when the first sleeve is in the extended locked position.

22. The syringe of claim 15, wherein the projecting means is positioned at the distal end of the first sleeve in the retracted position and near the proximal end of the first sleeve in the extended position.

23. The syringe of claim 22, wherein the second sleeve is located on the proximal end of the first sleeve and is moveable between an extended position and an extended locked position.

24. The syringe of claim 15, wherein the elongate slot extends the entire length of the first sleeve and includes a means for retaining the projecting means therein when the first sleeve is in the extended position.

25. A safety syringe, comprising
a syringe having proximal and distal ends, a barrel section extending therebetween, and a needle attached to the distal end of the barrel section,
a locating ring attached to the distal end of the barrel section and including a projecting means extending outwardly therefrom,
ends movable over said barrel section between a retracted position wherein the needle is exposed and an extended position wherein the needle is surrounded, said first sleeve including an elongate slot therein extending proximally from the distal end of said first sleeve and wherein said projecting means extends therethrough,
a second sleeve having proximal and distal ends movable over said first sleeve wherein said second sleeve and said locating ring cooperate to maintain the first sleeve in the retracted position, and
a hinge means on said second sleeve to releaseably retain said projecting means therein when said first sleeve is in the retracted position.

26. The syringe of claim 25, wherein the elongate slot has a proximal end and includes an enlarged slot on the proximal end thereof to retain the first sleeve in the extended position.

27. The syringe of claim 26, wherein the second sleeve is proximally movable from the distal end of said first sleeve to a location proximal to the enlarged slot on the first sleeve.

28. The syringe of claim 26, wherein the first sleeve includes an annular groove proximal to the enlarged slot and wherein the second sleeve is engaged therein when the first sleeve is in the extended position.

29. The syringe of claim 25, wherein the second sleeve is rotationally and movably positioned on the distal end of the first sleeve when the first sleeve is in the retracted position and wherein the second sleeve is engaged near the proximal end of the first sleeve when the first sleeve is in the extended position.

30. The syringe of claim 25, wherein the proximal end of the elongate slot has an enlarged slot to lock the projecting means therein when the first sleeve is in the extended position.

31. The syringe of claim 25, wherein said projecting means is releasably positioned in a slot located on the second sleeve when the first sleeve is in the retracted position and wherein the projecting means is releasable from said slot by the rotational movement of said second sleeve.

32. The syringe of claims 26, wherein said hinge means engages an annular groove located proximal to the enlarged slot when the first sleeve is in the extended position.

* * * * *